United States Patent [19]

Lauks

[11] Patent Number: 5,009,766

[45] Date of Patent: Apr. 23, 1991

[54] METAL OXIDE ELECTRODES

[75] Inventor: Imants R. Lauks, Morrisville, Pa.

[73] Assignee: I-Stat Corporation, Princeton, N.J.

[21] Appl. No.: 608,601

[22] Filed: Oct. 30, 1990

Related U.S. Application Data

[63] Continuation of Ser. No. 153,189, Feb. 8, 1988, which is a continuation of Ser. No. 390,445, Aug. 2, 1988, which is a continuation of Ser. No. 489,851, Mar. 2, 1990.

[51] Int. Cl.$^5$ .................................... G01N 27/46
[52] U.S. Cl. ................................ 204/419; 204/433; 204/291; 204/400; 204/403; 204/153.21; 204/153.12; 435/817; 435/291
[58] Field of Search ............... 204/419, 433, 291, 400, 204/403, 153.21, 153.12; 435/817, 291

[56] References Cited

U.S. PATENT DOCUMENTS

| 3,751,296 | 8/1973 | Beer | 204/290 F X |
| 3,778,307 | 12/1973 | Beer | 204/290 F X |
| 3,840,443 | 10/1974 | Beer | 204/290 F X |
| 4,012,296 | 3/1977 | Stephens et al. | 204/98 |
| 4,392,927 | 7/1983 | Fabian et al. | 204/98 |
| 4,589,959 | 5/1986 | Nakamatsu et al. | 204/98 |

OTHER PUBLICATIONS

Henry Freiser, "Ion-Selective Electrodes in Analytical Chemistry", vol. 1, pp. 1-2, (1979).
Henry Freiser, "Ion-Selective Electrodes in Analytical Chemistry", vol. 2, pp. 175-176, (1980).
H. M. N. H. Irving, "Compendium of Analytical Nomenclature", pp. 168-169.
Masanori Okuyama et al., Jpn. J. Appl. Phys., vol. 18, No. 8, pp. 1633-1634, (1979).
Eita Kinoshita et al., Talanta, vol. 33, No. 2, pp. 125-134, (1986).
Tadayuki Matsuo et al., Sensors and Actuators, 1, pp. 77-96, (1981).
Agner Fog et al., Sensors and Actuators, 5, pp. 137-146, (1984).
J. V. Dobson et al., Electrochimica Acta, vol. 21, pp. 527-533, (1976).
S. P. L. Sörensen, Biochimische Zeitschrift, pp. 131-145 (1909).
L. M. Schiavone et al., J. Electrochem. Soc., vol. 128, No. 6, pp. 1339-1342, (1981).
L. M. Schiavone et al., Appl. Phys. Lett., 35(10), pp. 823-825, Nov. 15, 1979.
L. Cammilli et al., Pace, vol. 1, pp. 448-457, Oct.-Dec. 1978.
I. M. Kolthoff et al., Societe Chimique Neerlandaise, Tome, XLIV, pp. 113-120, (1925).
Stanley M. F. Yuen, "Electrochemical Characteristics of Anodic and Sputtered Iridium Oxide Films", Aug. 1982.
N. F. deRooij et al., Proc. Int. Conf. Nijmegen, pp. 156-165, (1980).
T. Katsube et al., Sensors and Actuators, 2, pp. 399-410, (1982).

Primary Examiner—John F. Niebling
Assistant Examiner—Arun S. Phasge
Attorney, Agent, or Firm—Pennie & Edmonds

[57] ABSTRACT

An electrode for measuring the activity of ionic species. The electrode comprises a material which is chemically sensitive to at least one ionic species. The material comprises an insulating component and a conductive component of lower resistivity than the insulating component. The insulating component has a density of proton binding sites sufficiently large to be sensitive to the ionic species. The conductive component comprises particles, the size of which are sufficiently small to modify the bulk conductive properties such that the susceptibility of the particles to redox interference in the operation of the electrode is decreased, while maintaining sufficient conductivity to operate in Faradaic electrode configurations. Illustratively, the insulating component is tantalum oxide, zirconium oxide or aluminum oxide and the conductive component is iridium, platinum, ruthenium, palladium, rhodium or osmium oxide.

20 Claims, 2 Drawing Sheets

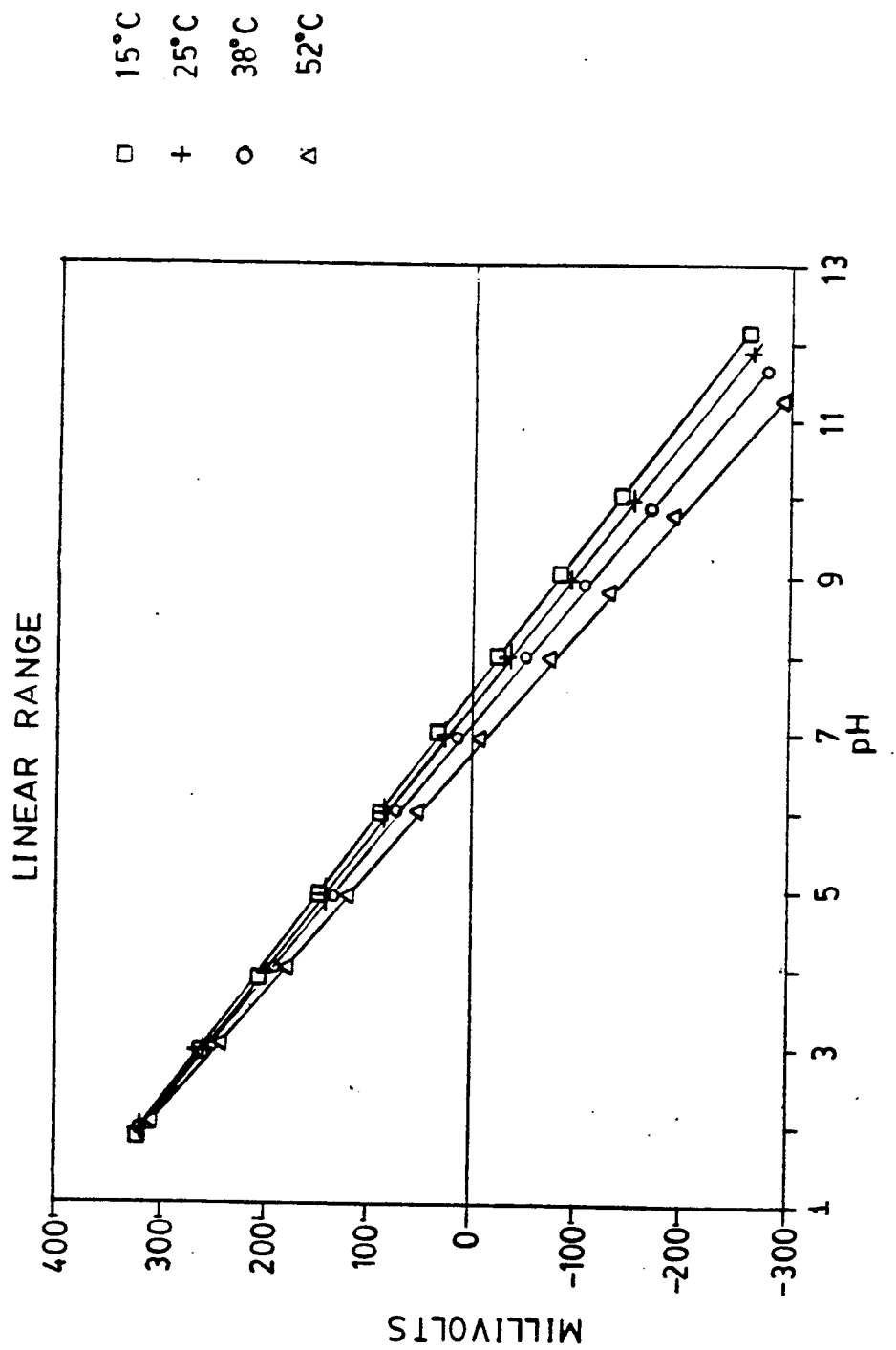

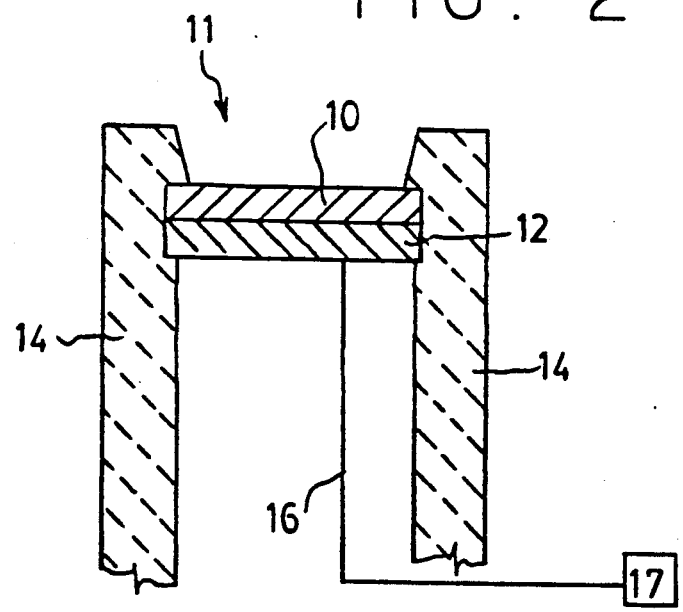

METAL OXIDE ELECTRODES

This is a continuation of application Ser. No. 153,189, filed Feb. 8, 1988, which is a continuation of application Ser. No. 390,445, filed Aug. 2, 1988, which is a continuation of application Ser. No. 489,851, filed 3/2/90.

FIELD OF THE INVENTION

This invention relates to electrodes for measuring chemical characteristics. More particularly, these electrodes are sensitive to one or more ionic species such as hydrogen ions.

BACKGROUND OF THE INVENTION

Numerous types and configurations of ion sensitive electrodes are known to those skilled in the art. Such electrodes typically comprise a composition which generates an electric potential as a result of an electrochemical reaction when in contact with a solution containing the ionic species to be detected. Under certain conditions, the Nernst equation expresses the functional relationship between the magnitude of this electric potential and the ion concentration. In designing accurate electrodes, it is critical that the electrode exhibit close to the ideal Nernstian response over a large ionic concentration range. Further, the electrode potential should respond quickly to changes in ion concentration.

A wide variety of materials has been used or proposed for use in connection with the detection of ionic species. Considerable investigative effort continues to be spent on the identification and evaluation of additional electrode materials for such purposes. To produce an ion sensitive electrode having good commercial utility, it is desirable that the ion sensitive electrode demonstrate good long term electrochemical stability. More specifically, the electrical response of such material upon exposure to a particular concentration of a given ionic species should not vary significantly over long periods of time, on the order of, for example, months or years. However, an electrode material may require a significant period of time in which to equilibrate or "temper" prior to reaching a state of equilibrium from which long term deviations will be acceptably small. Therefore, it is desirable that the time to equilibrate the electrode be of as short a duration as possible.

The electrode material should have good physical resiliency and strength. In this regard, the electrode materials should not be subject to breakage upon rough handling and should not exhibit diminished electrochemical capabilities if mishandled.

Finally, in view of the trend towards the miniaturization of instrumentation, it is also desirable that the material and means of construction of the electrode allow it to be manufactured with very small physical dimensions. Such microfabrication capability increases the utility and versatility of the electrode.

The concentration of hydrogen ions in a solution, commonly referred to as pH, is an example of a chemical characteristic measured by such electrodes. The field of pH measurement, which dates back to the early 1900,'s, (see S. P. L. Sorensen, Biochem Z. Vol. 21, 131 and 201 (1909)), has been reviewed extensively, notably in the well-known books by R. G. Bates, *The Determination of pH*, 2nd edition (Wiley, New York, 1973) and D. J. G. Ives and G. J. Janz (eds.), *Reference Electrodes* (Academic Press, New York, 1961).

Certainly the most widely used device for pH measurement is the glass electrode. Because it has been studied thoroughly for several decades, its performance characteristics are well understood on the fundamental level. The glass pH electrode offers the advantages of a wide range of response, freedom from oxidation-reduction ("redox") and other interferences, and attainment of the ideal Nernstian response slope of 59 mV/pH unit. Despite these advantages, there are certain materials and design limitations (e.g., high impedance and the need for an internal aqueous phase) which preclude the straightforward microminiaturization and production-level micro-fabrication of glass pH electrodes.

Metal oxide electrodes are better suited for microfabrication. This class of electrochemical systems dates back to the antimony/antimony-oxide electrode (see J. M. Kolthoff and B. D. Hartong, Rec. Trav. Chim., Vol. 44, 113 (1925)), and has subsequently come to include a variety of examples.

Iridium oxide electrodes have clearly emerged as the most attractive metal oxide electrode. An iridium oxide electrode, for example, has been reported to have been used in connection with a pH-triggered Pace Maker. See, Cammilli et al., "Preliminary Experience With a pH-Triggered Pace Maker," *PACE*, Vol. 1, pp. 448–457 (1978). This work was performed prior to the published discovery of sputtered iridium oxide by W. C. Dautremont-Smith in 1979. See L. M. Schiavone and W. C. Dautremont-Smith, *Applied Physics Letters*, Vol. 35, p. 823 (1979) and *Journal of the Electrochemical Society*, Vol. 128, p. 1339 (1981). The preparation of anodic iridium/iridium oxide pH electrodes has also been described. See, for example, Katsube et al., "pH Sensitive Sputtered Iridium Oxide Films," *Sensors and Actuators*, Vol. 2, No. 4, p. 399 (1982); De Rooij et al., "The Iridium/Anodic Iridium Oxide Film (Ir/AIrOF) Electrode as a pH Sensor." in N. F. De Rooij and P. Bergveld, *Monitoring of Vital Parameters During Extracorporeal Circulation*, Proc. Int. Conf. Nijmegen, p. 156 (1980). However, the anodic iridium oxide electrode disclosed by De Rooij exhibits an undesirable super Nernstian electrochemical response. Moreover, it is known that anodic iridium oxides are unstable in chemically harsh environments. See Yuen, *Chemical Characteristics of Anodic and Sputtered Iridium Oxide Films*, Masters Thesis, University of Pennsylvania (August, 1982). Chemically oxidized iridium oxide surfaces are similarly unstable. See Dobson et al., *Electrochemica Acta*, Vol. 21, pp. 527–533 (1976).

In addition to iridium oxide, other oxide systems have been considered. For example, A. Fog and R. P. Buck, *Sensors and Actuators*, Vol. 5, p. 137 (1984) discusses the use of platinum, ruthenium, osmium, tantalum, and titanium oxides. Further, J. V. Dobson et al., Ibid. discusses the use of rhodium and zirconium oxides. Palladium oxide studies have been reported by E. Kinoshita et al., "Talanta," Vol. 33, p. 125 (1986).

Each of the above-described metal oxides except tantalum oxide and zirconium oxide is conductive and is used to measure pH in a Faradaic configuration in which a chemical change at the electrode generates a potential. Hydrogen ions are exchanged backwards and forwards between the solution and the metal oxide at a rate governed by Faraday's law to establish a thermodynamic equilibrium and a stable interface potential. Since the metal oxide is conductive, the electrical potential generated in the metal oxide by virtue of the above electrochemical reaction is constant throughout the metal oxide and can be measured by making metallic contact to the back side of the oxide.

To varying degrees, all metal/metal-oxide pH electrodes exhibit problems with redox interference. It seems that the susceptibility of a metal oxide to redox interference is to some degree correlated with the conductivity of the metal oxide such that the factors which make a metal oxide sufficiently conductive for use in a Faradaic electrode result in significant redox interference.

In contrast, insulating metal oxides, which are not capable of supplying substantial output current, tend to exhibit relatively little redox interference. However, because of their high impedance, such oxides are useful only in non-Faradaic electrode configurations which operate without substantial output current from the metal oxide. One such configuration is the ion sensitive field effect transistor (ISFET) electrode. Again the electrode is brought into contact with a solution containing the ionic species to be measured. In this configuration, the potential generated by the ion sensitive material is applied to the gate of a field effect transistor. The ISFET operates to modulate its drain to source current in response to the electric field associated with the gate's potential, without drawing significant current from the electrode. Thus, the ISFET operates on the capacitive effect of charge at the oxide-solution interface upon a transistor structure on the other side of the oxide film. Two materials that appear to be best for pH ISFET use in terms of range of response, stability, sensitivity and freedom from interference are aluminum oxide and tantalum oxide (see T. Matsuo et al., "Sensors and Actuators," Vol. 1, p. 77 (1981)), both of which are commonly considered to be insulators and are routinely used as passivants in electron devices and Faradaic electrochemical sensors.

Unfortunately, FET based devices are relatively complicated and more costly to fabricate than simple Faradaic pH electrodes.

It is desirable to have a pH sensitive material, capable of generating substantial output current without exhibiting redox interference. Conventional metal oxides seem incapable of achieving that end.

SUMMARY OF THE INVENTION

It has been discovered that by properly combining at least one insulating material having a density of binding sites sufficiently large to be sensitive to the ionic species or analyte (such as an insulating metal oxide) and at least one Group VIIIB conductive metal oxide (such as iridium or platinum oxide) a chemically sensitive electrode is created which has a sufficiently low output impedance for use in simple configurations such as Faradaic electrodes, yet does not have the substantial redox interference commonly associated with conductive metal oxides. Accordingly, a simple, inexpensive, and accurate pH measurement system, capable of microfabrication, is provided.

According to the process of the present invention, the conductive and insulating components are combined in a manner which modifies the fundamental bulk properties of the conductive oxide. This is accomplished by controlling the morphology of the mixture, i.e. by controlling the size of the particle of the conductive oxide component within the mixture. It has been found that by ensuring that the particle size of the conductive component is sufficiently small, redox interference is reduced while providing adequate output current to operate in simple Faradaic electrode configurations. In the preferred embodiment, the conductive component is alloyed to the insulating component.

DESCRIPTION OF THE DRAWINGS

These and other objects, features and advantages of the invention will be more readily apparent from the following detailed description of the preferred embodiment of the invention in which:

FIG. 1 is a graph which illustrates the ideal Nernstian response of the metal oxide electrode of the present invention.

FIG. 2 is a cross-sectional view of an ion sensitive electrode in accordance with one embodiment of the present invention.

DETAILED DESCRIPTION OF THE DRAWINGS

Ion sensitive electrodes in accordance with the present invention, including membrane electrodes, comprise a conductive metal oxide combined with an insulating material in such a manner that the fundamental bulk conductive properties of the conductive oxide are modified to reduce the redox current which distorts the Nernstian response and therefore the accuracy of the measurement. More particularly, the electrode of the present invention comprises a Group VIIIB metal oxide and an insulating material having a density of proton binding sites sufficient to provide the sensitivity required matrixed in such a way so as to reduce the density of states at the Fermi level of the conductive metal oxide.

The above described combination provides an ion selective electrode having a fast Nernstian ion response and reduced redox interference while maintaining a high level of conductivity at the conductor, long term electro-chemical stability, reduced stabilization time required to equilibrate fresh electrodes, resistance to corrosion and chemical attack, low impedance, and easy adaptation for miniaturization and a variety of electrode configurations.

The electrode material of the present invention may be prepared in a variety of ways known to those skilled in the art. However, the electrodes must be prepared in a manner such that the morphology of the mixture is closely controlled. More particularly, the electrode material must be prepared so that the particle size of the conductive metal oxide in the mixture is reduced enough to minimize redox interference while providing adequate conductivity to permit the electrode to function as a Faradaic electrode. In contrast, an electrode consisting of a simple mixture of a conductive metal oxide and an insulating material or metal oxide, for example, the ROTO films (ruthenium oxide, tantalum oxide) described in Trasatti and O'Grady, "Advances in Electrochemistry and Electrochemical Engineering", Vol. 12, p. 200, results in an electrode with no improvement in pH sensing properties since the bulk conductive properties of the conductive metal oxide are maintained.

The reduction in particle size of the conductive metal oxide is sufficient that the particles no longer exhibit the bulk properties of the conductive metal oxide, specifically the bulk conductivity. The bulk conductivity property of the conductive metal oxide provides for the rapid electronic exchange which promotes redox reactions. The bulk conductivity property depends on the number of conductive electrons which, in turn, relates to the density of states of the Fermi level. By reducing the particle size, the density states at the Fermi level are reduced and the conductive metal oxide does not exhibit the bulk conductive properties of the material.

In the alternative, the electrode material may be prepared by alloying the conductive metal oxide to the insulating material. The amount of redox interference is reduced while maintaining sufficient conductivity to support an electrode in a Faradaic configuration.

The amount of conductivity the material should exhibit is dependent upon the application, preferably upon the impedance of the measurement circuit since the impedance of the material should be less than the impedance of the measuring circuit. For example, if the impedance of the measuring circuit is $10^{12}$ ohms, the impedance of the material is preferably less than about $10^{10}$ ohms.

The insulating material used in the electrode of the present invention is of the type in which the surface of the material readily exchanges protons. Proton exchange and, in particular, the level of sensitivity in the electrode material to changes in ionic concentration, is related to the density of proton binding sites in the material. The greater the density of proton binding sites the more rapid the proton exchange on the surface of the material and the greater the sensitivity of the material to the ionic concentration. Preferably the density of sites for proton exchange in the insulating material is greater than $10^{13}/cm^2$.

A preferred insulating material is an insulating metal oxide. For the determination of hydrogen ion concentration, i.e., the determination of pH, tantalum, zirconium and aluminum oxides are good examples of insulating meta oxides which exhibit excellent surface pH response characteristics.

The conductive metal oxide utilized in the electrode of the present invention is preferably selected from the Group VIIIB oxides, specifically, iridium, ruthenium, platinum, palladium, rhodium and osmium oxides.

Although the metal oxide electrode may be prepared by any manner in which the particle size is controlled, preferably the metal oxide is prepared through the process of sputtering the metal oxide on a conductive surface. Through such factors as the temperature of the substrate, the amount of bias and the rate of deposition, the particle size can be controlled. Sputtering techniques are described in Chopra, K. L., *Thin Film Phenomena*. This technique enables the production of dimensionally small ion sensitive electrodes using known microlithographic techniques.

The metal oxide electrode of the present invention may be used in conjunction with catalytic or enzymatic layers to measure an ionic species and calculate the concentration of specific components in the ambient. This may be accomplished by placing at least one layer of material between the metal oxide composition and the ambient to be sensed so as to detect a change of the concentration of ionic species in the layer resulting from exposure of that layer to the ambient. Through the change in the concentration of the ionic species sensed by the metal oxide electrode of the present invention, the concentration can be determined of a species of interest in the ambient.

EXAMPLES

Table I sets forth measurements of resistivity, pH drift, sensitivity, oxidant interference and reductant interference for one insulating metal oxide, tantalum oxide, and two conductive metal oxides, iridium oxide and platinum oxide, and two metal oxides of the present invention, iridium-tantalum oxide and platinum-tantalum oxide.

Electrodes of the materials identified in Table I were prepared by sputter deposition on metallized substrates.

As shown in Table I, the tantalum oxide electrode displayed very high resistivity and large drift making pH measurements impossible. Electrodes constructed of pure iridium oxide exhibited an ideal pH response slope, but also exhibited substantial oxidant interference of 1 to 1.5 pH units and reductant interference of 1.7–3.4 pH units. Likewise, the platinum oxide electrode as reported by Fog and Buck (see A. Fog and R. P. Buck, "Sensors and Actuators," Vol. 5, p. 137 (1984)), displayed similar properties with an oxidant and reductant interference of 1.7 pH units. The amount of interference is measured by placing the electrode in a redox neutral environment of a known value of pH and subsequently placing the electrode in the solution having the same pH. The change of value of pH is reflective of the amount of redox interference.

However, the iridium-tantalum and platinum-tantalum oxide electrodes of the present invention exhibited an ideal Nernstian response (58–59 mv) with a reduction in drift, a reduction in the oxidant interference and a reduction in the reductant interference. More particularly, the iridium tantalum oxide electrode of the present invention exhibited a resistivity of $5 \times 10^{12}$ ohms/cm, a small drift of approximately 0.1, an oxidant interference of 0.3–0.6 and a reductant interference of 0.02–0.05 which constitute reductions in interference by factors of three and 70, respectively. Similarly, the platinum-tantalum oxide electrode of the present invention exhibited resistivity of $1.5 \times 10^{13}$ ohm/cm with a drift of 0.1, an oxidant interference of 0.1–0.2 and a reductant interference of 0.3–0.6. Further analysis of the pH response of the mixed metal oxide electrodes of the present invention showed that the pH sensitivity scales quantitatively with absolute temperature as predicted by the Nernst equation. See FIG. 1 which shows a Nernstian response at temperatures of 15, 25, 38 and 52 degrees Celsius.

Table II shows the results of organic redox interference tests performed on an iridium-tantalum oxide electrode of the present invention. As is evident from Table II, the quantity of organic redox interference which can corrupt the electrochemical measurement of pH is minimal.

The iridium-tantalum oxide electrode used to obtain the favorable results set forth in Tables I and II was prepared having an iridium-tantalum molar ratio of approximately 0.09 and a particle size less than 50 angstroms. While the above results were obtained by maintaining a particle size of 50 angstroms, preferred embodiments include particle sizes of less than 100 angstroms where the limiting case of a particle size of zero is an amorphous alloy. In addition, the mixed metal oxide electrode of the present invention is not limited to the above examples, but can be made of other combinations of insulating metal oxides, such as tantalum, zirconium and aluminum oxide, and conductive metal oxides, such as iridium, platinum, ruthenium, palladium, rhodium and osmium oxides.

The mixed metal oxide described may be used in a variety of electrode configurations.

FIG. 2 depicts in cross-section an ion sensitive electrode in accordance with one embodiment. Sensing layer 10, comprising a conductive oxide alloyed with an insulating material, is prepared in contact with a conductive underlayment 12, such as a metallic underlayment, which is in contact with conductive lead 16. The entire assembly of sensing layer 10, metallic underlayment 12 and lead 16 is preferably chemically and electrically isolated from the ionic environment 11 by inert packaging means 14. Such isolation does not include one or more surfaces of sensing layer 10. The inert packaging means may be any of a wide variety of materials which are capable of isolating the foregoing assembly of sensing layer, underlayment and lead from the environment as required. Such inert packaging means should also be capable of withstanding, without degradation, the chemical, thermal and ionic environment into which the article is to be placed. Such material may be any of a wide variety of plastics, laminates, ceramics, or other materials capable of achieving the foregoing goals.

the foregoing determination. The magnitude of the electrochemical interaction between sensing layer 10 and the ions of the environment 11 is dependent in a generally Nernstian fashion upon the activity of the ions in that environment. In most cases, such activity is approximated closely by the concentration of ions in the environment. Accordingly, such concentration may be determined through application of the Nernst equation to the generated potential as transmitted by lead 16.

Although almost any type of metallic underlayment 12 may be used, for sputtered iridium/tantalum oxide, the underlayment may comprise iridium metal, a silicon wafer, or many other electrically transmissive species. Optionally the conductive oxide and insulating material have no metal atoms in common with metallic underlayment 12.

While the invention has been described in connection with several specific embodiments, it is evident that numerous alternatives, modifications, and variations will be apparent to those skilled in the art in light of the foregoing description.

TABLE I

| Substance | resistivity (ohm-cm) | drift ph units in 24 hrs. | sensitivity mV/pH unit | oxidant interference (ph unit) | reductant interference (ph unit) |
|---|---|---|---|---|---|
| tantalum oxide | $-10^{14}$ | very large | indeterminable | | |
| iridium oxide (amorphous) | $-10^2$ | $-0.15$ | 58–59 | 1.0–1.5[a] | 1.7–3.4[b] |
| iridium/tantalum oxide | $-5 \times 10^{12}$ | $-0.10$ | 58–59 | 0.3–0.6[a] | 0.02–0.05[b] |
| platinum oxide | | | (47)[d] | (1.7)[e] | (1.7)[e] |
| platinum-tantalum oxide | $-1.5 \times 10^{13}$ | $-0.1$ | 58–60 | 0.1–0.2[c] | 0.3–0.6[b] |

Legend for Table I
[a]Measured in 0.01 M $K_2Cr_2O_7$ solution at pH2.
[b]Measured in 0.0005 M ascorbate solution at pH7.
[c]Measured in 0.03 M $K_2Cr_2O_7$ solution at pH2.
[d]Value reported by Fog and Buck.
[e]Value reported by Fog and Buck. The exact meaning of "redox interference is not defined, but 0.01 M solutions of $Fe(CN)_6$ and $Fe(CN)_6$ were employed in the measurement.

TABLE II

| | Organic Redox Interference Study with Iridium-Tantalum Oxide pH Electrodes | | |
|---|---|---|---|
| | | (± denotes standard deviation for electrodes) | |
| Species | Concentration (mM) | Interference at pH = 7.4 (pH units) | Interference at pH = 2.0 (pH units) |
| pyruvic acid | 10.0 | 0.002 ± 0.003 | −0.020 ± 0.030 |
| lactic acid | 100.0 | −0.009 ± 0.003 | 0.020 ± 0.020 |
| oxalic acid | 2.6 | −0.003 ± 0.005 | −0.010 ± 0.030 |
| salicylic | 110.0 | −0.007 ± 0.008 | 0.005 ± 0.019 |
| succinic acid | 6.1 | −0.030 ± 0.060 | −0.020 ± 0.010 |
| oxalacetic acid | 6.1 | −0.002 ± 0.005 | 0.007 ± 0.021 |
| L-ascorbic acid | 12.0 | 0.050 ± 0.040 | −0.070 ± 0.050 |
| acetominophen | 12.0 | 0.005 ± 0.005 | −0.009 ± 0.019 |

In accordance with the practice of an embodiment of this invention, environment 11 comprises one or more ionic species to be measured such as hydrogen ions. The electrode assembly of FIG. 2 is placed into contact with the ions of the environment whereupon an electrochemical reaction between sensing layer 10 and the ions of the environment 11 takes place to generate an electrical potential. This potential is transmitted via metallic underlayment 12 and lead 16 to appropriate potential sensing or measurement means 17. As will be appreciated by those skilled in the art, a source of reference potential, not shown, may also be required or preferred. The metallic underlayment 12 and lead 16 are chemically and electrically insulated from the environment 11 by packaging means 14 so as to avoid secondary electrochemical reactions between the environment 11 and underlayment 12 or lead 16 which would interfere with

What is claimed:

1. A metal oxide electrode sensitive to hydrogen ions comprising:
   a mixture of at least one insulating material having a density of binding sites sufficiently large to be sensitive to hydrogen ions, and at least one conductive metal oxide selected from the Group VIIIB metal oxides,
   wherein the size of the particles of conductive metal oxide in said mixture is sufficiently small as to not exhibit bulk conductive properties, thereby reducing the susceptibility of said mixture to redox interference, while the molar ratio of said conductive metal oxide to said insulating material is sufficiently large than the resistivity of said mixture is in the range of $10^{10}$ to $10^{14}$ ohm-cm, whereby the electrode, as a whole, has sufficient conductivity to operate in a Faradaic configuration.

2. The electrode of claim 1 wherein said insulating material is an insulating metal oxide with a resistivity of at least $10^{14}$ ohm-cm.

3. The electrode of claim 2 wherein said mixture is deposited on a surface of a substrate by sputter coating.

4. The electrodes of claim 3 wherein said metal oxide mixture has no metal atoms in common with said substrate.

5. The electrode of claim 1 further comprising:
at least one layer of material placed over said mixture, said layer of material being reactive with an analyte to be measured,
wherein reaction with said analyte to be measured produces a change in concentration of hydrogen ions which is sensed by said mixture.

6. The electrode of claim 1 wherein the size of conductive metal oxide particles is in the range of less than 100 angstroms.

7. The electrode of claim 1 wherein particle size is controlled in a manner such that the insulating material and conductive metal oxide form an amorphous alloy.

8. The electrode of claim 1 wherein said conductive metal oxide is selected from the group consisting of iridium, platinum, ruthenium, palladium, rhodium, and osmium oxides.

9. The electrode of claim 1 wherein said insulating material is selected from the group consisting of aluminum oxide, zirconium oxide and tantalum oxide.

10. The electrode of claim 1 wherein the insulating material has density of hydrogen ion binding sites greater than $10^{13}/cm^2$.

11. An electrode for measuring pH comprising:
a mixture of a first component which is conductive in bulk form, and a second component having a substantially greater resistivity in bulk form than that of said first component, said second component having a redox-interference-free surface response to hydrogen ions, said first component being present in said mixture in sufficiently small particle size so as to modify its bulk conductive properties enough that it does not affect the redox-interference-free surface response of said second component to hydrogen ions,
wherein the molar ratio of said first component to said second component is sufficiently large that the resistivity of said mixture is in the range of $10^{10}$ to $10^{14}$ ohm-cm, whereby the electrode, as a whole, has sufficient conductivity to operate as a pH sensing electrode.

12. The electrode of claim 11 wherein said first component is a conductive metal oxide and said second component is an insulating metal oxide.

13. The electrode of claim 11 wherein said first component is iridium oxide.

14. The electrode of claim 11 wherein said second component is selected from the group consisting of aluminum oxide, zirconium oxide, and tantalum oxide.

15. The electrode of claim 13 wherein said second component is tantalum oxide.

16. The electrode of claim 11 wherein the size of the particles of the first component are in the range of less than 100 angstroms.

17. The electrode of claim 11 wherein particle size is controlled in a manner such that the insulating material and conductive metal oxide form an amorphous alloy.

18. The electrodes of claim 11 wherein said mixture is deposited on a substrate by sputter coating.

19. The electrode of claim 18 wherein said mixture has no metal atoms in common with said substrate.

20. The electrode of claim 11 further comprising:
at least one layer of material placed over said mixture, said layer of material being reactive with an analyte to be measured,
wherein reaction with said analyte to be measured produces a change in concentration of hydrogen ions which is sensed by said mixture.

* * * * *